United States Patent
Sugaya et al.

(10) Patent No.: US 9,377,470 B2
(45) Date of Patent: Jun. 28, 2016

(54) PROGNOSIS DIAGNOSIS METHOD AND PROGNOSIS DIAGNOSIS KIT FOR SEPSIS OR MULTIPLE ORGAN FAILURE

(75) Inventors: Takeshi Sugaya, Hyogo (JP); Eisei Noiri, Tokyo (JP); Kent Doi, Tokyo (JP)

(73) Assignees: Takeshi Sugaya, Itami-shi (JP); THE UNIVERSITY OF TOKYO, Tokyo (JP)

( * ) Notice: Subject to any disclaimer, the term of this patent is extended or adjusted under 35 U.S.C. 154(b) by 1171 days.

(21) Appl. No.: 13/383,565

(22) PCT Filed: Jul. 15, 2010

(86) PCT No.: PCT/JP2010/061957
§ 371 (c)(1),
(2), (4) Date: Feb. 2, 2012

(87) PCT Pub. No.: WO2011/007823
PCT Pub. Date: Jan. 20, 2011

(65) Prior Publication Data
US 2012/0135433 A1 May 31, 2012

(30) Foreign Application Priority Data
Jul. 15, 2009 (JP) ................................ 2009-167191

(51) Int. Cl.
G01N 33/68 (2006.01)
G01N 33/53 (2006.01)

(52) U.S. Cl.
CPC ............ *G01N 33/6872* (2013.01); *G01N 33/53* (2013.01); *G01N 2800/26* (2013.01)

(58) Field of Classification Search
None
See application file for complete search history.

(56) References Cited

U.S. PATENT DOCUMENTS

| | | | |
|---|---|---|---|
| 6,794,154 B1 | 9/2004 | Yamanouchi et al. | |
| 7,592,148 B1 | 9/2009 | Yamanouchi et al. | |
| 8,034,551 B2 * | 10/2011 | Sugaya et al. | 435/4 |
| 2004/0185503 A1 | 9/2004 | Yamanouchi et al. | |
| 2005/0101016 A1 | 5/2005 | McIntyre | |
| 2007/0243560 A1 * | 10/2007 | Yamanouchi et al. | 435/7.1 |
| 2010/0248377 A1 * | 9/2010 | Hess et al. | 436/86 |
| 2012/0028292 A1 * | 2/2012 | Hess et al. | 435/29 |

FOREIGN PATENT DOCUMENTS

| | | |
|---|---|---|
| JP | 11-242026 | 9/1999 |
| JP | 2001-037486 | 2/2001 |
| JP | 2004-155788 | 6/2004 |
| JP | 2006-526027 | 11/2006 |

OTHER PUBLICATIONS

HyCult Biotechnology, "HBT Elisa Test Kits for Liver Fatty Acid Binding Protein", 2003, retrieved from http://deltaclon.es/pdf/HK405.pdf on Jan. 22, 2015, 2 pages.*

Josephy et al., "The Horseradish Peroxidase-catalyzed Oxidationof 3,5,3',5'-Tetramethylbenzidine", The Journal of Biological Chemistry vol. 257, No. 7, Issue of Apr. 10, pp. 36694675, 1982.*

Kajimo et al. "Urinary fatty acid—binding protein as a new clinical marker of the progression of chronic renal disease", J Lab Clin Med (2004), 23-30.*

Bone et al., "American College of Chest Physicians/Society of Critical Care Medicine Consensus Conference: Definitions for sepsis and organ failure and guidelines for the use of innovative therapies in sepsis", Critical Care Medicine, Vo. 20, No. 6, Jun. 1992, pp. 864-874.

Thijs et al., "Time course of cytokine levels in sepsis", Intensive Care Med (1995) 21:S258-S263.

Van Der Poll et al., "Antiinflammatory Cytokine Responses during Clinical Sepsis and Experimental Endotoxemia: Sequential Measurements of Plasma Soluble Interleukin (IL)-1 Receptor Type II, IL-10, and IL-13", Journal of Infectious Diseases (1997) 175:118-122.

Nakamura et al., "The involvement of urinal L-FABP and the effect of PMF-F treatment in septic shock patients" Kidney-Dialysis Center, Shin Matsudo Chuo Sogo Hospital, and Institute of Physical and Chemical Research, Nov. 19, 2004 , Abstract O-65 (one page).

Nakamura et al., <Zoeizai ni yori AKI ni Tsuite no Topic> Saikin no Chiken L-FABP• NAC- Statin- hANP• Ace Sogaiyaku Hoka, Naika, Jul. 1, 2008, vol. 102, No. 1, p. 109 to 113.

* cited by examiner

*Primary Examiner* — Christine Foster
(74) *Attorney, Agent, or Firm* — Knobbe Martens Olson and Bear, LLP

(57) ABSTRACT

Disclosed are: a prognosis diagnosis method which can diagnose the prognosis of a patient suffering from sepsis or sepsis-related multiple organ failure in a simple manner and with high accuracy and a prognosis diagnosis kit for use in the prognosis diagnosis method. The prognosis diagnosis method comprises: a first detection step of detecting a liver fatty acid-binding protein contained in urine collected from a subject with a specific antibody; a second detection step of treating the urine with a Redox reagent such as hemin and detecting a liver fatty acid-binding protein contained in the treated urine with the specific antibody; and a comparison step of comparing a detection value obtained in the first step with a detection value obtained in the second step. It is determined that the larger the detection value obtained in the second step compared to that in the first step, the worse the prognosis.

3 Claims, 3 Drawing Sheets

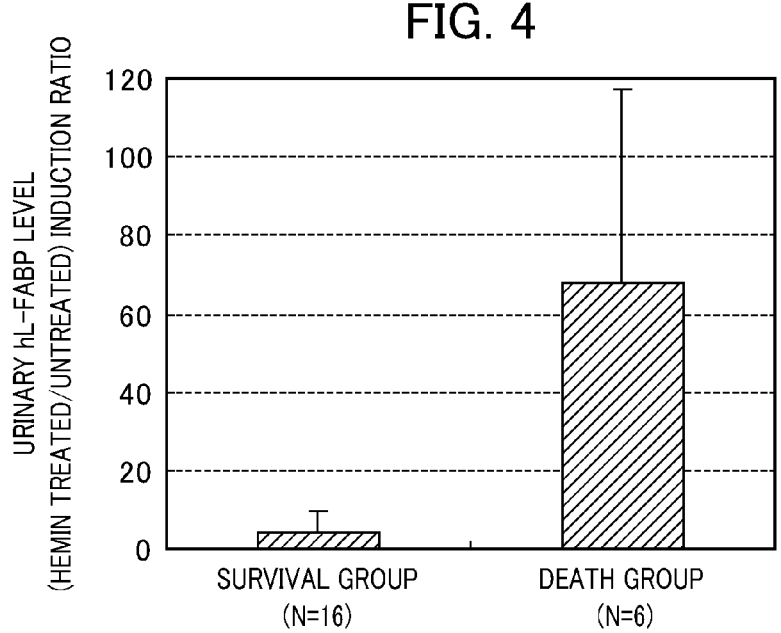
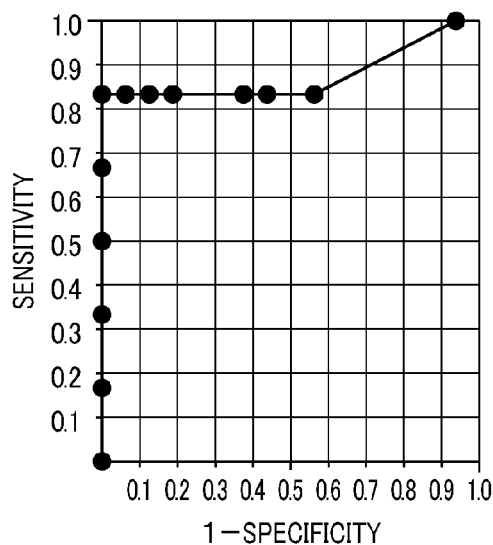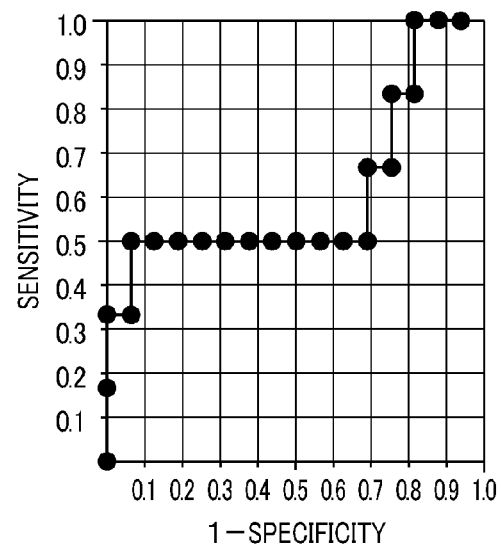

PROGNOSIS DIAGNOSIS METHOD AND PROGNOSIS DIAGNOSIS KIT FOR SEPSIS OR MULTIPLE ORGAN FAILURE

This application is the U.S. National Phase under 35 U.S.C. §371 of International Application PCT/JP2010/061957, filed Jul. 15, 2010, designating the U.S., and published in Japanese as WO2011/007823 on Jan. 20, 2011, which claims priority to Japanese Patent Application No. 2009-167191, filed Jul. 15, 2009, the entire contents of which are incorporated herein by reference.

TECHNICAL FIELD

The present invention relates to a prognostic diagnostic method of sepsis or sepsis-related multiple organ failure, and a kit for prognostic diagnosis for use in the prognostic diagnostic method.

BACKGROUND ART

Sepsis is a systemic inflammatory response syndrome (SIRS) associated with an infection, and is defined according to requirements for 4 items of: body temperature (being lower than 36° C., or higher than 38° C.); heart rate (being more than 90 times/min); respiration (respiratory rate being more than 20 times/min, or $PaCO_2$ being less than 32 mmHg); and number of leukocytes (being no less than $12,000/mm^3$, or no greater than $4,000 mm^3$, or appearance of no less than 10% juvenile cells), that is, sepsis is considered to be positive when 2 or more items among these meet the requirements (see Nonpatent Document 1). In Nonpatent Document 1, seriousness of sepsis is defined according to bases subsequent to sepsis such as dysfunction of organs, lowering of blood flow, decrease in blood pressure, tissue circulatory disorder and the like. The seriousness is greater in the order of sepsis; severe sepsis; and septic shock, and the greater seriousness leads to multiple organ failure (MOF).

At present, fluid resuscitation, administration of an antibiotic, blood purification therapy, control of the blood glucose level, administration of corticosteroid or activated protein C, and the like are performed in treatment of sepsis. In addition, it is important to diagnose prognosis of patients who suffered from sepsis or sepsis-related multiple organ failure for deciding treatment principles hereafter. In particular, severe patients who must be admitted to an intensive care unit (ICU) are postulated to fall within any of entire stages from sepsis to multiple organ failure; therefore, a capability of determining a marker that correlates with final clinical outcome (i.e., survival or death) when admitted to the ICU is believed to be useful for selection of treatment strategy.

Conventionally, several blood markers have been reported to reflect the prognosis of sepsis. For example, Nonpatent Document 2 reports that there is a correlation between the content of IL-1 in blood and poor prognosis of a septic patient. However, there is also a report that is contrary to Nonpatent Document 2, and thus it has not been established as a prognostic diagnostic method. In addition, Nonpatent Document 3 reports that the content of IL-10 in blood is high in septic patients with poor prognosis, whereas it is significantly decreased in septic patients with favorable prognosis. However, an increase of IL-10 can be detected only 80% of septic shock patients; therefore, the detection is not satisfactory for a prognostic diagnostic method.

On the other hand, fatty acid binding proteins (FABPs) are a group of proteins having a molecular weight of about 15 kD, which are present in cytosol and have an ability of bind to fatty acids. Although FABP is believed to participate in regulation of metabolic enzyme systems by way of intracellular transfer or accumulation of fatty acids, details of their physiological function are unclear. At least seven molecular species have been known as FABPs such as liver-type (L-FABP), intestine-type (I-FABP), myocardium-type (H-FABP), brain-type (B-FABP), skin-type (C-FABP/E-FABP), adipocyte-type (aP2) and peripheral nerve cell-type (myelin P2), and their primary structures were determined. Any of these have a fatty acid binding capacity, and a region having a well conserved sequence can be fond in part. Taking into consideration these and other findings, they are believed to form a family evolved from a common ancestor gene; however, as a whole they have different structures with one another, and exhibit each specific tissue distribution. It should be noted that the designation such as liver-type or intestine-type means the tissue in which the FABP was initially found, and does not necessarily mean that the FABP is present only in the tissue.

Recently, it is reported that L-FABP included in the urine from septic shock patients significantly increases as compared with that in healthy individuals (see Nonpatent Document 4). In addition, Nonpatent Document 4 also reports that the urinary L-FABP level significantly decreases by carrying out a blood purification therapy (endotoxin adsorption: PMX) in the patients of the survival group among septic shock patients, whereas the urinary L-FABP level does not decrease in the patients of the death group; therefore, the urinary L-FABP can be a candidate of a marker for deciding an effect of blood purification therapy. However, the disclosure in this report is not practically applicable as a prognostic diagnostic method since there is a prerequisite of carrying out a blood purification therapy, and thus the prognosis cannot be diagnosed based merely on the of urinary L-FABP level.

Nonpatent Document 1: Crit. Care Med., 20: 864-874, 1992

Nonpatent Document 2: Thijs, L. G. and Hack, C. E., Inten. Care Med., 21: S258-263, 1995

Nonpatent Document 3: Van der Poll, J. Infect. Dis., 175: 118-122, 1997

Nonpatent Document 4: Abstract of the 24th Japanese Society for Apheresis (November, 2004) Session Number: 0-65

DISCLOSURE OF THE INVENTION

Problems to be Solved by the Invention

The present invention was made in view of the foregoing conventional circumstances, and an object of the invention is to provide a prognostic diagnostic method capable of diagnosing the prognosis of a patient suffering from sepsis or sepsis-related multiple organ failure in a convenient manner and with high accuracy diagnosis, and a kit for prognostic diagnosis for use in the prognostic diagnostic method.

Means for Solving the Problems

The inventors thoroughly investigated in order to solve the foregoing problems. As a result, it was found that: (i) when collected urine is treated with a redox reagent such as hemin (i.e., chloro(porphyrinato)iron(III) complex), immunoreactivity of urinary L-FABP is enhanced; and (ii) as the degree of enhancement (induction ratio) is greater, the prognosis of a patient suffering from sepsis or multiple organ failure is worse. More specifically, the present invention provides the following aspects.

A first aspect of the invention is a prognostic diagnostic method of sepsis or multiple organ failure, the method including: a first detection step of detecting L-FABP contained in urine collected from a subject with a specific antibody; a second detection step of treating the urine with a redox reagent, and detecting L-FABP contained in the treated urine with the specific antibody; and a comparison step of comparing a detected value in the first step with a detected value in the second step.

A second aspect of the invention is the prognostic diagnostic method according to the first aspect, in which, in the comparison step a ratio of the detected value in the second detection step to the detected value in the first detection step is compared with a threshold value.

A third aspect of the invention is the prognostic diagnostic method according to the first or second aspect, in which, the redox reagent is hemin.

A fourth aspect of the invention is a kit for prognostic diagnosis for use in the prognostic diagnostic method according to any one of the first to third aspects.

A fifth aspect of the invention is a kit for prognostic diagnosis according to the fourth aspect, which includes a specific antibody for L-FABP, and a redox reagent.

Effects of the Invention

According to the present invention, provided are a prognostic diagnostic method capable of diagnosing the prognosis of a patient suffering from sepsis or sepsis-related multiple organ failure in a convenient manner and with high accuracy, and a kit for prognostic diagnosis for use in the prognostic diagnostic method.

BRIEF DESCRIPTION OF THE DRAWINGS

FIG. 4 shows a view illustrating results of comparison of the ratio (induction ratio) with respect to the hL-FABP level detected in the urine from a subject when admitted in ICU, of the hL-FABP level detected after treating the same urine sample with a treatment liquid containing 0.5 mM hemin, on a survival group and a death group.

FIG. 5A shows a view illustrating an ROC curve on the induction ratio.

FIG. 5B shows a view illustrating an ROC curve on CRP.

PREFERRED MODE FOR CARRYING OUT THE INVENTION

[Prognostic Diagnosis Method]

Figure 1A:
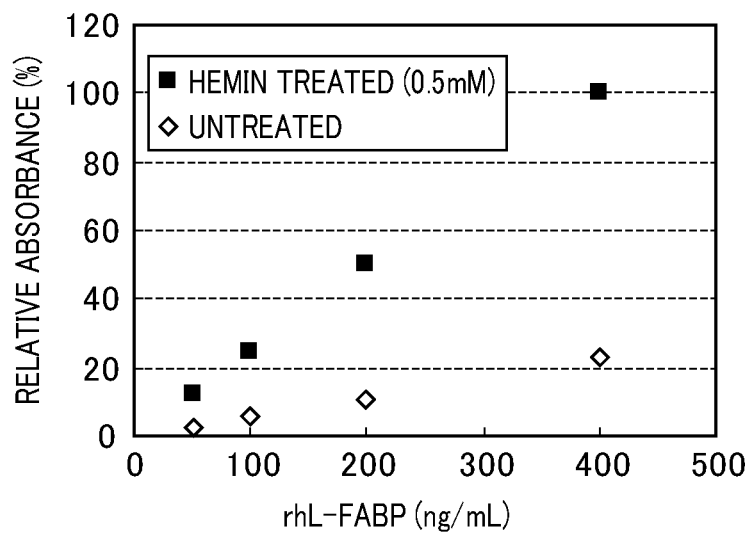
FIG. 1A shows a view illustrating an immunoreactivity enhancing effect on recombinant human L-FABP when hemin was used as a redox reagent.

The prognostic diagnostic method according to the present invention includes: a first detection step detecting L-FABP contained in the urine collected from a subject with a specific antibody; a second detection step of treating the urine with a redox reagent, and detecting L-FABP contained in the treated urine with the specific antibody; and a comparison step of comparing a detected value (detection result) in the first step with a detected value (detection result) in the second step.

(First Detection Step)

In the first detection step, L-FABP contained in the urine collected from a subject is detected by an immunochemical method with a specific antibody for L-FABP.

The antibody can be prepared using L-FABP as an immunizing antigen. When a naturally occurring L-FABP is used as an immunizing antigen, L-FABP can be purified from liver, kidney or the like. The purification may be carried out as described in the following according to a method described in a document of Kelvin et al., (J. Biol. Chem., 263: 15762-15768, 1988) or the like. More specifically, a cytoplasmic fraction obtained by subjecting an extirpated organ to ultracentrifugation after being homogenized is fractionated by gel filtration, anion exchange chromatography or the like to purify through selecting a fraction containing L-FABP based on the molecular weight or fatty acid-binding activity as a marker. Furthermore, SDS polyacrylamide electrophoresis is carried out for additional purification, or for identification as to whether a single band was given. Thereafter, the amino acid composition and the N-terminal amino acid sequence of the purified protein are determined, and they are compared with reported compositions and sequences to confirm as to whether or not an intended molecular species was obtained.

A fatty acid-binding activity of L-FABP may be easily determined using, for example, a fluorescent probe such as ANS (1,8-anilinonaphthalenesulfonic acid). The fluorescent probe will have increased fluorescence intensity by binding to a highly hydrophobic region of L-FABP such as a lipid binding site. For example, after adding ANS to a solution containing L-FABP and mixing the solution, a fluorescence intensity (excitation wavelength: 372 nm; fluorescence emission wavelength: 480 nm) may be measured. Alternatively, a fatty acid-binding activity of L-FABP can be also determined by using RI-labeled fatty acid.

Since L-FABP is known to be highly homologous among human, mouse, pig, cattle and rat, with a homology of no less than 90% at amino acid level, for example, mouse L-FABP can be used as an antigen for obtaining an antibody that binds to human L-FABP. In this case, an advantage of ease in preparing an antigen can be attained.

L-FABP used as an immunizing antigen may be a recombinant protein produced by a genetic engineering technique. Since the amino acid sequence and the gene sequence of L-FABP were already reported (Veerkamp and Maatman, Prog. Lipid Res., 34: 17-52, 1995), recombinant L-FABP can be prepared by, for example, designing a primer based on such information, cloning a cDNA by a PCR method from an appropriate cDNA library or the like, and carrying out gene recombination using the cDNA.

Alternatively, a fragment of L-FABP, a synthetic peptide having a partial sequence thereof or the like bound as needed to a carrier high-molecular substance (bovine serum albumin, hemocyanin or the like) may be used as an immunizing antigen.

The specific antibody for L-FABP may be any one of an antiserum, a polyclonal antibody, a monoclonal antibody and the like.

The antibody preferably has high specificity, and desirably does not substantially cross-react with, for example, a myocardium-type fatty acid binding protein (H-FABP). In order to obtain an antibody having higher specificity, use of a highly purified antigen to give high purity is desired.

For preparing the antibody, the purified antigen prepared as described above is inoculated to a warm-blooded animal to permit immunization. Examples of the immunized warm-blooded animal include mammals (rabbit, sheep, rat, mouse, guinea pig, horse, pig and the like), and birds (chicken, duck, goose and the like). In the case of a rabbit, for example, an emulsion prepared by emulsifying about 100 μg to 1 mg of the antigen in about 1 ml of physiological saline and Freund's complete adjuvant is inoculated into a dosal region or under the skin of hind limb palm, and Freund's incomplete adjuvant is used in place of the Freund's complete adjuvant in the emulsion for use in the second and the following inoculation, executed for immunization three to eight times at 2 to 4 weeks intervals. The animal is used about 7 to 12 days after the final inoculation. In the case of a mouse, 10 to 30 μg/animal of the antigen per inoculation is usually used for immunization carried out subcutaneously, intraperitoneally or intravenously three to eight times at about 2 weeks intervals, and the animal is used about 2 to 4 days after the final inoculation.

The polyclonal antibody can be prepared by collecting blood from the animal immunized as described above, fractionating the serum (antiserum), and recovering an Ig fraction from the obtained antiserum. For example, an IgG fraction is recovered from the antiserum by affinity chromatography using a Protein G column, or the like, thereby capable of obtaining a polyclonal IgG.

A monoclonal antibody is produced from a hybridoma obtained by fusion of antibody-producing cells collected from an immunized animal with immortalized cells. As the animal to be immunized for obtaining a monoclonal antibody, mouse and rat may be suitably used. The hybridoma may be produced according to the method of Kohler and Milstein (Nature, 256: 495-897, 1975) as in the following. More specifically, antibody-producing cells (spleen cells, lymph node cells, etc.,) are collected from the animal immunized as described above, and cell fusion of these is permitted with appropriate immortalized cells. As the immortalized cell, for example, a cell strain of myeloma cells (NSI—Ag4/1, Sp2/O—Ag14, etc.,) may be suitably used. The myeloma cell is preferably of nonsecretory type which does not produce per se an antibody or H chain or L chain of immunoglobulin. Also, the myeloma cell preferably has a selection marker which enables fused hybridoma to be selected from unfused myeloma cells in a selection medium. For example, a cell strain having 8-azaguanine resistance (hypoxanthine-guanine-phosphoribosyl transferase deficiency), thymidine kinase deficiency or the like as a selection marker is often used.

The cell fusion is carried out by adding an appropriate fusion promoter such as polyethylene glycol. The cell fusion is preferably carried out at a proportion of about 10 antibody-producing cells per the immortalized cell, and can be suitably performed at a cell density of the antibody-producing cells of about $10^6$ cells/ml.

After the cells subjected to the fusion treatment are appropriately diluted, they are cultured 1 to 2 weeks in a selection medium. For example, when myeloma cells that are resistant to 8-azaguanine are used, unfused myeloma cells die when cultured in a HAT (hypoxanthine, aminopterin, thymidine) medium, and unfused antibody-producing cells also die due to restriction of the division cycle; however, only fused cells can survive in the selection medium while continuing the cell division.

After culturing in the selection medium, the presence of the intended antibody may be detected by carrying out, for example, enzyme immunoassay on the supernatant, and then a hybridoma producing a monoclonal antibody that recognizes the target antigen can be selected by cloning according to a limiting dilution method. When selected, a hybridoma (monoclonal antibody) having suitable properties such as the antibody titer, the antibody class and subclass, the affinity with the antigen, the specificity, the epitope and the like may be selected. The class of the monoclonal antibody is preferably IgG, in general.

The monoclonal antibody-producing hybridoma is transplanted into, for example, the abdominal cavity of the animal used for immunization, and the ascites fluid is collected after a certain period of time. Thus the intended monoclonal antibody can be isolated from the ascites fluid. Alternatively, the hybridoma is cultured in an appropriate medium for animal cell culture, and the monoclonal antibody may be isolated from the culture fluid. Also, once the intended hybridoma is obtained, a gene encoding the monoclonal antibody may be obtained therefrom, whereby production of the intended monoclonal antibody is enabled by permitting expression in a suitable host according to a common gene recombination technique.

Separation and purification of the antibody may be carried out according to a common purification method in which, for example, ammonium sulfate precipitation, gel chromatography, ion exchange chromatography, affinity chromatography and the like are combined as needed.

Detection and quantitative determination of the L-FABP (antigen) in urine using the specific antibody obtained as described above may be carried out by employing a well-known method such as enzyme immunoassay (EIA), chemiluminescent immunoassay, or electroluminescence assay. Furthermore, a method such as radioimmunoassay (RIA) or fluoroimmunoassay may be also employed as desired. Specifically, for example, a competition method in which an antibody and a labeled antigen are used, a sandwich EIA method in which two types of monoclonal antibodies or polyclonal antibodies (or a monoclonal antibody and a polyclonal antibody) having different recognition site for the antigen are used in combination, and the like may be employed. In these assay methods, the antigen or the antibody is supported on a suitable support (gel particle, cellulose particle, polyacrylamide gel, physical adsorbent material (glass, styrene based resin) or the like) if necessary. For example, a solid phase method in which an antigen or antibody is adsorbed on a solid phase such as a plate or beads made from polystyrene are often employed. Also, a Western blotting method, for example, may be employed for the detection.

In the immunochemical method descried above, the antibody and/or the antigen may be used after labeling as needed. For the labeling, an enzyme (peroxidase, alkaliphosphatase, etc.,), a luminous substance (acridinium ester, isoluminol, luciferin, etc.,) as well as radioisotope ($^{124}$I, $^{14}$C, $^{3}$H), a fluorescent substance (fluorescein isothiocyanate, etc.,), or the like may be used. Also, a method in which a biotin label is combined with streptavidin may be employed.

(Second Detection Step)

In the second detection step, the aforementioned urine collected from a subject is treated with a redox reagent, and then L-FABP contained in the treated urine is detected and quantitatively determined in a similar manner to the above first detection step with a specific antibody. As described above, immunoreactivity of urinary L-FABP is enhanced by treating the urine with a redox reagent. This event is speculated to result from improvement of the binding property of L-FABP with the antibody since the treatment with a redox reagent eliminates chemical modification which included in urinary L-FABP in part e.g., at cysteine residues and the like (Peter Dormann et al., J. Biol. Chem., 268: 16286-16292, 1993). It should be noted that this enhancing effect is observed also on recombinant L-FABP.

The redox reagent is not particularly limited, and a well-known redox reagent may be used as long as it can lead to a chemical modification at a free amino acid residue of the protein (for example, SH group of cysteine) at around a neutral pH. Specific examples of the redox reagent include hemin, aluminum nitrate nonahydrate, ammonium perchlorate, ammonium peroxodisulfate, cesium nitrate, cerium(III) nitrate hexahydrate, cerium(III) diammonium nitrate tetrahydrate, calcium nitrate tetrahydrate, guanidine nitric acid salt, indium(III) nitrate trihydrate, diiodine pentoxide, lithium perchlorate trihydrate, lithium nitrate, lanthanum nitrate hexahydrate, lithium perchlorate, magnesium nitrate hexahydrate, magnesium perchlorate, potassium iodate, orthoperperiodic acid, potassium bromate, potassium nitrate, potassium perchlorate, rubidium nitrate, sodium iodate, sodium chloroisocyanurate, sodium bromate, sodium peroxodisulfate, sodium periodate, sodium perchlorate, sodium perchlorate monohydrate, trimethylphenylammonium bromide, ytterbium(III) nitrate tetrahydrate, zirconyl nitrate dihydrate, tris (2-carboxyethyl)phosphine hydrochloride (TCEP), and the like. Of these, at least one selected from the group consisting of hemin, tris(2-carboxyethyl)phosphine hydrochloride (TCEP), ammonium peroxodisulfate, calcium nitrate tetrahydrate, guanidine nitric acid salt and magnesium nitrate hexahydrate is preferred, and hemin is most preferred.

The treatment with a redox reagent may include, for example, mixing the urine collected from a subject and a treatment liquid containing a redox reagent, and allowing it to react for a predetermined time. The solvent of the treatment liquid may include Tris buffer, phosphate buffer, and the like. Also, the concentration of the redox reagent in the treatment liquid is preferably 0.1 to 100 mM. Although the reaction time is not particularly limited, it may be about 30 sec to 10 min.
(Comparison Step)

In the comparison step, the detected value in the first step (detection result) is compared with the detected value (detection result) in the second step. As described above, the treatment of the collected urine with a redox reagent enhances immunoreactivity of the urinary L-FABP, and greater degree of enhancement (induction ratio) suggests poor prognosis of the patient suffering from sepsis or multiple organ failure. Therefore, by comparing the detected value in the first step with the detected value in the second step to determined whether or not the induction ratio exceeds a threshold value, the prognosis can be diagnosed. This threshold value is predetermined from statistics of the induction ratios in the patients with favorable prognosis and the patients with poor prognosis. For example, the threshold value is predetermined by carrying out an ROC analysis (Receiver Operating Characteristic analysis) based on the induction ratios in the patients with favorable prognosis and the patients with poor prognosis, such that the sensitivity and the specificity both become no less than 80%, and the ROC Area Under the Curve (AUC: Area Under the Curve) preferably becomes no less than 0.8.
[Kit for Prognostic Diagnosis]

The kit for prognostic diagnosis according to the present invention is used for the prognostic diagnostic method described in the foregoing. The kit for prognostic diagnosis is exemplified by a support such as e.g., beads or a plate (96-well microplate, etc.,) on which an anti-L-FABP antibody was adsorbed/bound. In this case, the kit for prognostic diagnosis includes a specific antibody for L-FABP and a redox reagent in combination. The specific antibody may be a labeled antibody. With respect to the label, an antibody to which an enzyme such as peroxidase is bound (enzyme labeled antibody), a biotinylated antibody (biotin labeled antibody), and the like may be exemplified. Also, the redox reagent may be provided as a treatment liquid in a state being dissolved in a solvent. Furthermore, the kit for prognostic diagnostic may include a reagent required for EIA and the like (enzyme-labeled secondary antibody, color formation substrate, etc.,) in combination.

Also, a qualitative, semiquantitative, or quantitative measurement method based on an immunochromatography kit capable of rapidly and conveniently determining the results may be utilized.

EXAMPLES

Hereinafter, the present invention is explained in detail by way of Examples, but the present invention should not be construed to be limited thereto.

Example 1

Immunoreactivity-Enhancing Effect Achieved Using Recombinant Human L-FABP (rhL-FABP)

A treatment liquid (solvent: Tris buffer) containing 0.5 mM hemin or 10 mM tris (2-carboxyethyl)phosphine hydrochloride (TCEP) was mixed with a rhL-FABP standard sample (50 to 400 ng/mL) in an equal volume, and the mixture was left to stand still at room temperature for 10 min. Thereafter, the absorbance was detected by an ELISA method (hL-FABP measurement kit, manufactured by Immuno-Biological Laboratories Co., Ltd.). For a base line, a mixture of the Tris buffer used as the solvent for the treatment liquid, and a rhL-FABP standard sample was provided.

Figure 1B:
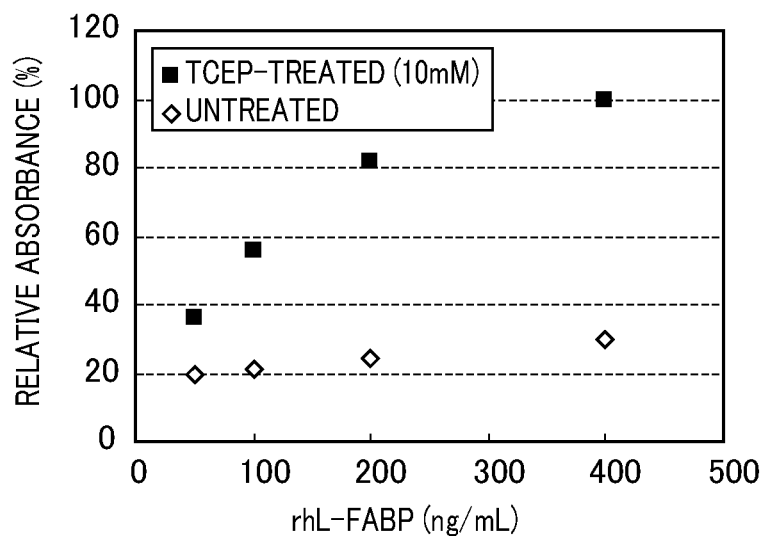
FIG. 1B shows a view illustrating an immunoreactivity enhancing effect on recombinant human L-FABP when TCEP was used as a redox reagent.

Results obtained when hemin was used as a redox reagent are shown in FIG. 1A, and results when tris (2-carboxyethyl) phosphine hydrochloride (TCEP) was used are shown in FIG. 1B. The FIG. 1A and FIG. 1B indicate in terms of the relative strength (%) provided that the absorbance of a mixture of the treatment liquid containing the redox reagent with 400 ng/mL of rhL-FABP was assumed to be 100%. As is seen from FIG. 1A and FIG. 1B, an effect of enhancing the immunoreactivity of any of the redox reagents was confirmed in proportion to the amount added. Also, it was reveled that hemin is more preferred in light of the linearity with respect to the dilution and minimization of the base line background.

Example 2

Relationship between Severity in Mouse CLP Model and Measurements of Urinary L-FABP Level First, in order to produce transgenic mice into which a human L-FABP gene was introduced (hL-FABP-Tg mouse), 13 or more-week-old BCF1 male mice were used for infertile mating and natural mating; 10 or more week-old-ICR female mice were used for embryo transplantation and for foster parent; 13 or more-week-old BDF1 male mice were used for mating; and 8 or more-week-old BCF1 female mice were used for ovum collection, respectively. The transgenic mice (B6C3F1 strain) thus obtained were backcrossed with a BALB/cA mouse to produce hL-FABP-Tg mice.

Next, using the hL-FABP-Tg mice, two types (severe and mild) of cecal ligation and puncture (CLP) model mice were produced to provide septic patient models exhibiting different severity. Specifically, under ether inhalation anesthesia, the hL-FABP-Tg mouse was subjected to laparotomy by ventral median incision, and the cecum roots were ligated using a 3-0 floss with the ileocecal valve being salvaged. Thereafter, using a 18-G needle (in the case of the severe model) or a 21-G needle (in the case of the mild model), puncture and perforation were performed over the entire cecal wall layer. The wound of abdominal wall incision was closed by single layer suture. The urine was collected three times of immediately after the surgery operation (0 time), 6 hours later and 18 hours later. Each urine was mixed with a treatment liquid (solvent: Tris buffer) containing 0.5 mM hemin in an equal volume, and the mixture was left to stand still at room temperature for 10 min. Thereafter, the hL-FABP level was measured by an ELISA method (hL-FABP measurement kit, manufactured by Immuno-Biological Laboratories Co., Ltd.).

Figure 2:
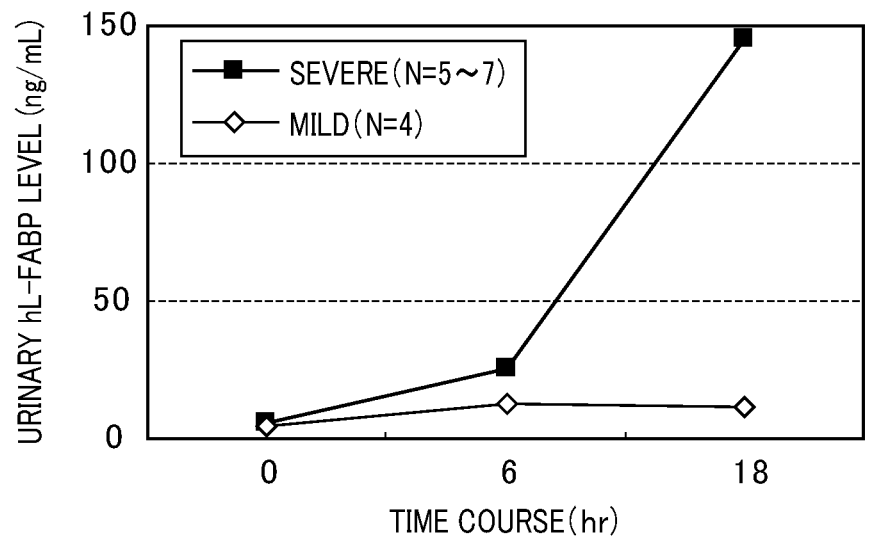
FIG. 2 shows a view illustrating measurements of the urinary hL-FABP level after subjecting the urine collected from CLP model mice with discrete severity to a treatment with hemin.

The measurements of urinary hL-FABP level of the severe model (N=7 at a time point of 6 hrs later, and N=5 at a time point of 18 hrs later due to the death of two animals) and the mild model (N=4 until 18 hrs later without death), respectively are shown in FIG. 2. As is seen from FIG. 2, the immunoreactivity of the urinary hL-FABP was significantly enhanced by the hemin treatment in the severe model mice; however, the immunoreactivity was almost unchanged in the mild model mice. This enhancing effect was found from very early stage, i.e., significant difference was already found on 6 hours after the surgery operation ($P<0.01$). The results indicate that diagnosis of prognosis at very early stage is enabled according to the method of the present invention.

Example 3

Figure 3:
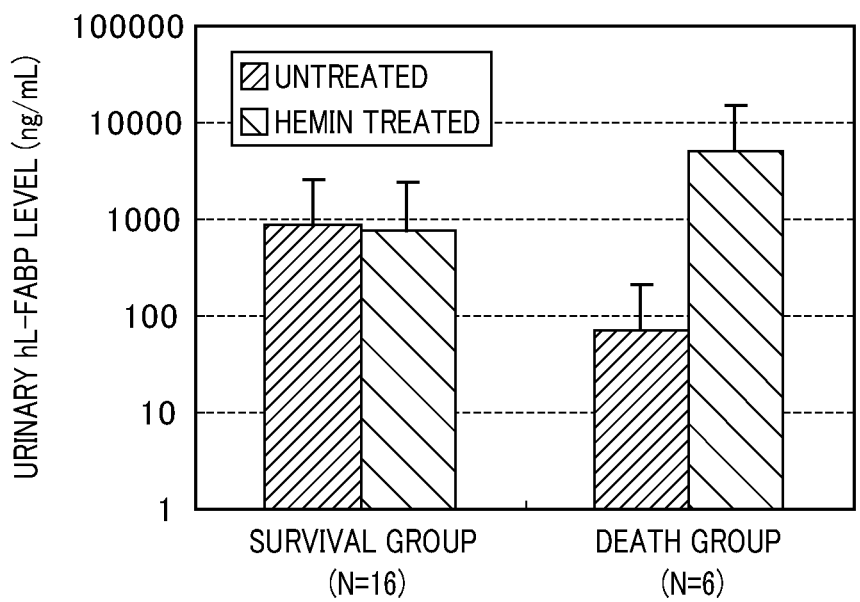
FIG. 3 shows a view illustrating results of comparison of the hL-FABP level detected in the urine from a subject when admitted in ICU, with the hL-FABP level detected after treating the same urine sample with a treatment liquid containing 0.5 mM hemin, on a survival group and a death group.

Relationship between Severity of ICU Patients and Measurements of Urinary hL-FABP Level Among the patients treated in the intensive care unit (ICU) of The University of Tokyo Hospital, the cases in which multiple organ failure of 2 or more organs was exhibited on admission, and initiation of blood purification therapy was suggested were adopted as subjects. The urine on admission was collected, and the hL-FABP level was measured by an ELISA method (hL-FABP measurement kit, manufactured by Immuno-Biological Laboratories Co., Ltd.). The same urine sample was mixed with a treatment liquid (solvent: Tris buffer) containing 0.5 mM hemin in an equal volume, and the mixture was left to stand still at room temperature for 10 min. Thereafter, the hL-FABP level was similarly measured. The measurements (ng/mL) of the urinary hL-FABP level in the untreated case, the measurements (ng/mL) of the urinary hL-FABP level in the hemin treatment case and the induction ratio in the survival group (N=16) and the death group (N=6) are shown in Table 1 below. In Table 1, the outcome and the clinical information of each patient are shown together with. Furthermore, summarized illustrations of the values in this Table with respect to the survival group and the death group are shown in FIGS. 3 and 4.

TABLE 1

| | | Untreated (ng/mL) | Hemin treated (ng/mL) | Induction ratio | Outcome | Clinical information |
|---|---|---|---|---|---|---|
| Survival group | 1 | 3879.5 | 2712.6 | 0.7 | Moved to other hospital | Gastrointestinal bleeding, Pneumoniae, Rapidly progressive kidney injury |
| | 2 | 1.0 | 5.8 | 5.7 | Remission | Septic shock |
| | 3 | 41.8 | 61.5 | 1.5 | Remission | Septic shock |
| | 4 | 1416.5 | 1030.8 | 0.7 | Remission | Intracerebral breeding, Extensive burn |
| | 5 | 6334.9 | 6168.2 | 1.0 | In hospital | Acute leukemia, GVHD, Infectious myocarditis |
| | 6 | 15.9 | 97.0 | 6.1 | Remission | Acute leukemia, Septic shock |
| | 7 | 616.5 | 469.9 | 0.8 | Moved to other hospital | Asphyxia, Postresuscitation following cardiopulmonary arrest |
| | 8 | 63.6 | 228.9 | 3.6 | Moved to other hospital | Gastrointestinal bleeding, Postresuscitation following cardiopulmonary arrest |
| | 9 | 135.1 | 276.1 | 2.0 | Moved to other hospital | Renal failure, Diabetic ketoacidosis |
| | 10 | 947.8 | 384.4 | 0.4 | Remission | Urinary tract infectious disease, Septic shock |
| | 11 | 0.8 | 0.7 | 0.8 | Remission | Duodenal perforation, Diffuse peritonitis |
| | 12 | 0.3 | 5.6 | 18.6 | Remission | Large bowel perforation, Diffuse peritonitis |
| | 13 | 0.4 | 1.0 | 2.4 | Remission | Post surgery for uterine leiomyoma, Large bowel perforation, Diffuse peritonitis |
| | 14 | 14.1 | 104.9 | 7.5 | Remission | Acute aortic dissection |
| | 15 | 45.9 | 253.7 | 5.5 | Remission | Acute left ventricular failure, Arrhythmia |
| | 16 | 17.4 | 222.6 | 12.8 | Remission | Small intestinal perforation, Diffuse peritonitis |
| | Average | 845.7 | 751.1 | 4.4 | | |
| | SD | 1771.1 | 1593.1 | 5.1 | | |
| Death group | 1 | 339.7 | 25325.0 | 74.6 | Death | Acute splenic infarction, Hepatic failure, Acute renal failure |
| | 2 | 12.8 | 18.1 | 1 | Death | Leg cellulitis |
| | 3 | 3.1 | 373.2 | 122 | Death | Large bowel perforation, Diffuse peritonitis |
| | 4 | 75.4 | 5039.6 | 67 | Death | Artificial heart infection, Septic shock |

TABLE 1-continued

|   | Untreated (ng/mL) | Hemin treated (ng/mL) | Induction ratio | Outcome | Clinical information |
|---|---|---|---|---|---|
| 5 | 3.1 | 365.7 | 119 | Death | Post surgery for aortic dissection, Bowel ischaemia |
| 6 | 0.3 | 7.4 | 25 | Death | Septic shock, Aspiration pneumonia, Ileus |
| Average | 72.4 | 5188.2 | 68.2 | | |
| SD | 134.0 | 10055.1 | 48.8 | | |

As is seen from Table 1 and FIG. 3, the hL-FABP level detected from the untreated urine was not significantly different between the survival group and the death group. However, the hL-FABP level detected after subjecting the urine sample to a treatment with a treatment liquid containing 0.5 mM hemin tended to be higher in the death group as compared with the survival group. In addition, as is seen from Table 1 and FIG. 4, the ratio (induction ratio) with respect to the hL-FABP level detected in the untreated urine, of the hL-FABP level detected after treating the same urine sample with a treatment liquid containing 0.5 mM hemin was significantly higher in the death group as compared with the survival group (P<0.01).

For reference, with respect to the same patient groups, acute kidney injury score (RIFLE; R: score 1, I: score 2, F: score 3, no injury: score 0) when admitted in the ICU and one week later, number of leukocytes, CRP, and execution of blood purification therapy was performed (CHDF, PMX; each score 1) are shown in Table 2 below.

TABLE 2

| | | RIFLE (on admission) | RIFLE (1 W) | Number of leukocytes | CRP | Existence of blood purification therapy |
|---|---|---|---|---|---|---|
| Survival group | 1 | 2 | 3 | 23200 | 1.06 | 1 |
| | 2 | 0 | 0 | 12300 | 3.05 | 1 |
| | 3 | 0 | 0 | 200 | 12 | 1 |
| | 4 | 3 | 3 | 33400 | 4.71 | 0 |
| | 5 | 3 | 3 | 16900 | 0.71 | 1 |
| | 6 | 1 | 1 | 100 | 7.93 | 1 |
| | 7 | 0 | 0 | 10800 | 1.15 | 0 |
| | 8 | 0 | 3 | 20400 | 0.14 | 0 |
| | 9 | 3 | 3 | 19800 | 0.3 | 0 |
| | 10 | 1 | 1 | 4100 | 3.18 | 0 |
| | 11 | 3 | 3 | 1400 | 21.14 | 0 |
| | 12 | 0 | 1 | 1500 | 2.51 | 2 |
| | 13 | 0 | 0 | 5200 | 14.57 | 1 |
| | 14 | 2 | 2 | 10000 | 0.21 | 1 |
| | 15 | 0 | 1 | 12700 | 0.2 | 0 |
| | 16 | 3 | 3 | 18700 | 1.3 | 0 |
| Death group | 1 | 3 | 3 | 40800 | 17.29 | 2 |
| | 2 | 3 | 3 | 32300 | 34.76 | 0 |
| | 3 | 2 | 2 | 16100 | 0.77 | 1 |
| | 4 | 1 | 1 | 12100 | 22.59 | 1 |
| | 5 | 1 | 3 | 12500 | 0.22 | 1 |
| | 6 | 0 | 0 | 8800 | 0.47 | 2 |

As is seen from Table 2, definite correlation was not found between the acute kidney injury score, the number of leukocytes, CRP, execution of blood purification therapy, and the clinical outcome.

Furthermore, in order to evaluate the accuracy of the prognostic diagnostic method according to the present invention, an ROC analysis was carried out. An ROC curve on the induction ratio is shown in FIG. 5A, whereas an ROC curve on CRP for the comparison is shown in FIG. 5B. As a result of the ROC analysis, the ROC Area Under the Curve (AUC) on FIG. 5A was 0.875, and the ROC Area Under the Curve on FIG. 5B was 0.609. Additionally, when the cut-off value was 20, sensitivity for the induction ratio was 0.83, and the specificity was 1.00.

From these results, it is proven that the prognosis of a patient suffering from sepsis or sepsis-related multiple organ failure is enabled in a convenient manner and with high accuracy diagnosis, according to the prognostic diagnostic method according to the present invention. Particularly, since a ratio of the L-FABP level detected in the urine treated with a redox reagent with respect to the L-FABP level detected in the untreated urine is used as a marker in the prognostic diagnostic method according to the present invention, it is advantageous in that necessity for measurement of creatinine in the urine for correction of the concentration in a urine sample, followed by calculation for the correction can be avoided.

The invention claimed is:

1. A method for determining a prognosis of sepsis or multiple organ failure, comprising:
    measuring a first level of liver-type fatty acid-binding protein (L-FABP) contained in a first portion of a urine sample obtained from a subject diagnosed as having sepsis or multiple organ failure with a specific antibody for liver-type fatty acid-binding protein (L-FABP), said first portion not being treated with hemin;
    treating a second portion of the urine sample with herein, and measuring a second level of L-FABP contained in the second portion with the specific antibody;
    determining an induction ratio as the ratio of the second level of L-FABP to the first level of L-FABP; and
    determining the prognosis of sepsis or multiple organ failure in the subject based on the induction ratio, wherein the subject is determined to have a lower likelihood of survival when the induction ratio exceeds a predetermined threshold value and conversely wherein the subject is determined to have a higher likelihood of survival when the induction ratio when the induction ratio is less than or equal to the predetermined threshold value.

2. The method of claim 1, wherein the treating is conducted under conditions where the concentration of the hemin in the second portion of the urine sample is 0.1 to 100 mM and for a time of about 30 sec to 10 min.

3. The method of claim 1, further comprising the steps of:
    selecting a treatment strategy for the subject, said treatment strategy comprising at least one treatment selected from the group consisting of fluid resuscitation, administration of an antibiotic, blood purification therapy, control of blood glucose level, and administration of corticosteroid or activated protein C; and
    administering, said treatment to the subject when the subject is determined to have a lower likelihood of survival based on the induction ratio exceeding the predetermined threshold value.

* * * * *